(12) United States Patent  
Ashman (10) Patent No.: US 6,402,518 B1
(45) Date of Patent: Jun. 11, 2002

(54) METHOD AND APPARATUS FOR PERFORMING RIDGE AUGMENTATION

(76) Inventor: Arthur Ashman, 153 Bayberry La., Westport, CT (US) 06880

(*) Notice: Subject to any disclaimer, the term of this patent is extended or adjusted under 35 U.S.C. 154(b) by 0 days.

(21) Appl. No.: 09/449,879

(22) Filed: Nov. 30, 1999

(51) Int. Cl.[7] .................................................. A61C 5/00
(52) U.S. Cl. .......................... 433/215; 433/173; 623/16
(58) Field of Search ................................ 433/167, 173, 433/174, 215; 606/53, 69, 70; 623/16

(56) References Cited

U.S. PATENT DOCUMENTS

| 4,251,215 A | * | 2/1981 | May et al. ............... 433/168.1 |
| 4,787,906 A | * | 11/1988 | Haris ........................... 623/16 |
| 4,820,306 A | * | 4/1989 | Gorman et al. ............... 623/16 |
| 5,073,114 A | * | 12/1991 | Detsch ..................... 433/228.1 |
| 5,093,179 A | * | 3/1992 | Scantlebury et al. ........ 433/215 |
| 5,372,503 A | | 12/1994 | Elia |
| 5,397,235 A | | 3/1995 | Elia |
| 5,433,607 A | * | 7/1995 | Schmid et al. ............... 433/173 |
| 5,695,338 A | * | 12/1997 | Robert ........................ 433/215 |
| 5,700,479 A | * | 12/1997 | Cungren ...................... 623/11 |
| 5,795,592 A | * | 8/1998 | Tonetti ........................ 424/484 |
| 5,824,088 A | * | 10/1998 | Kirsch .......................... 623/16 |
| 5,839,899 A | * | 11/1998 | Robinson .................... 433/215 |
| 6,019,764 A | * | 2/2000 | Bartee .......................... 606/86 |
| 6,030,218 A | * | 2/2000 | Robinson .................... 433/173 |
| 6,071,284 A | * | 6/2000 | Fox .............................. 606/80 |

* cited by examiner

Primary Examiner—Ralph A. Lewis
(74) Attorney, Agent, or Firm—Darby & Darby (57) ABSTRACT

A method and apparatus for augmenting an endentulous alveolar ridge of a patient comprises the steps of (1) making a provisional denture-stent with a hollow space on the underside to account for the width, height and extent of the desired augmentation; (2) making an incision in, and reflecting, the gingiva where the augmentation is desired; (3) inserting bone graft material on the cortical plate; (4) suturing the gingiva; and (5) inserting the provisional stent over the bone graft material.

35 Claims, 5 Drawing Sheets

METHOD AND APPARATUS FOR PERFORMING RIDGE AUGMENTATION

FIELD OF THE INVENTION

The present invention relates to dental surgical procedures in general and, more particularly, to a method and apparatus for augmenting a patient's alveolar ridge or jaw bone using bone graft material.

BACKGROUND OF THE INVENTION

According to a National Survey on Oral Health, conducted by the National Institute of Dental Research, approximately 42 percent of Americans over 65 years of age and four percent of those 35 to 64 are totally edentulous. Moreover, those over 65 years old who are not totally edentulous have nevertheless lost an average of 12 of their 28 teeth, and persons aged 55 to 64 have lost an average of 9 of their 28 teeth.

When an extracted or otherwise missing tooth is not immediately grafted or replaced with an implant, atrophy of the jaw bone occurs over time. Consequently, individuals who have been partially edentulous for an extended period of time are left with an atrophic alveolar ridge that can not securely support a denture. Furthermore, the edentulous individual faces deteriorated aesthetics and a compromised ability to chew leaving the quality of the individual's oral life in an unfortunate state.

Figure 1:
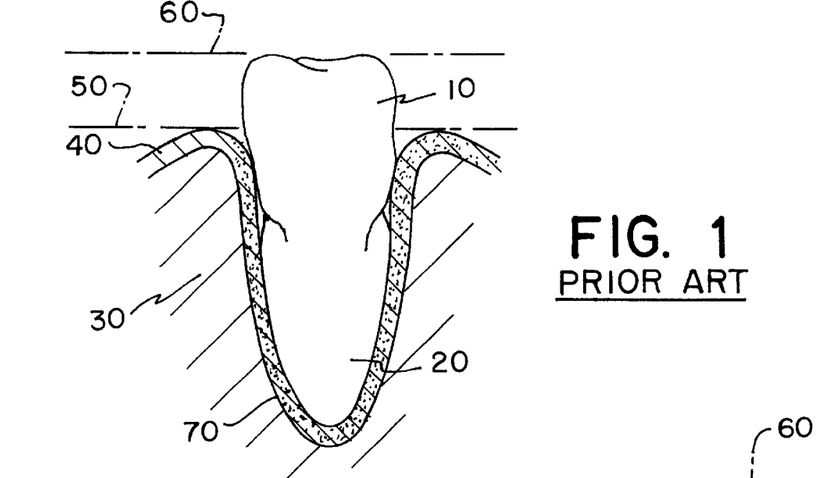
FIG. 1 is a cross-sectional view of a tooth crown and root prior to extraction from the alveolar ridge.
Figure 2:
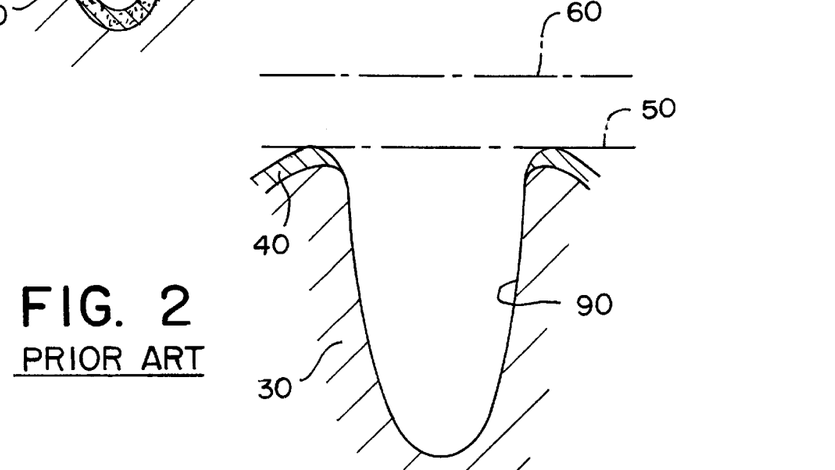
FIG. 2 is cross sectional view of the alveolar ridge following the extraction of the root illustrated in FIG. 1.
Figure 3:
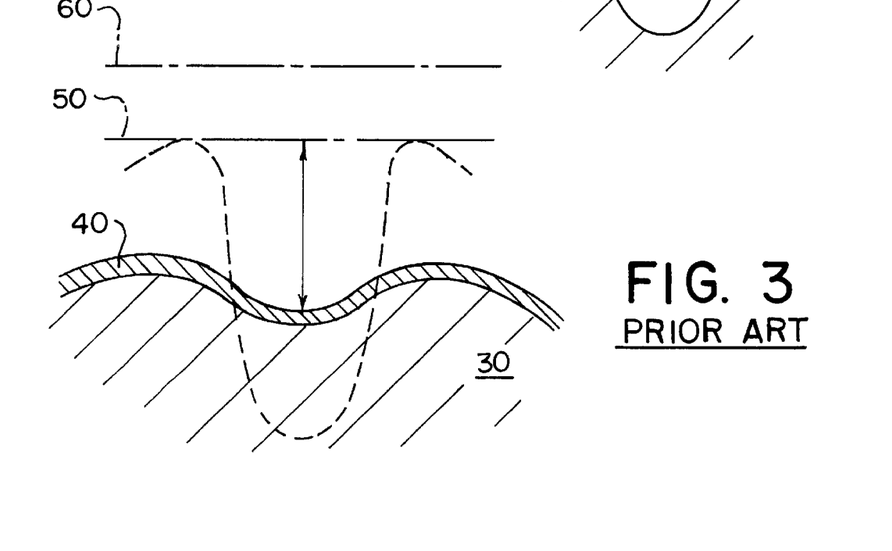
FIG. 3 is a cross-sectional view an atrophied alveolar ridge two years following the root extraction illustrated in FIG. 2.

FIGS. 1 through 3 illustrate the deteriorating effect of tooth extraction on the alveolar ridge. FIG. 1 illustrates a tooth of a patient, comprised of a crown 10 and root 20 seated in the alveolar bone or jaw bone 30. The buccal and lingual portions of the alveolar bone are surrounded by a layer of tissue known as the gingiva or gum 40. The crown 10 and root 20 are supported by the elevated portion of the alveolar ridge or jaw bone 30 and gingiva 40 which, in the ideal case, hold all of the teeth in place such that a level gum line 50 and crown line 60 are maintained. When such a tooth or series of teeth become infected, damaged or otherwise hygienically dangerous, such that the extraction of the crown 10 and root 20 are required, the root is removed from the alveolar bone 30 by separating the surface of the root 20 from the periodontal membrane 70.

FIG. 2 represents the portion of the jaw bone shortly after extraction of the crown 10 and root 20. As is shown, the periodontal membrane clots such that bleeding ceases and a socket 90 remains in the alveolar bone 40 in the shape of the extracted root 20.

The buccal and lingual portions of the alveolar bone 30 are composed of soft trabecular bone which has the unique characteristic of being capable of absorbing the shocks caused by the movement of teeth during speech, eating, etc. The removal of a tooth and the resulting absence of frequent bone pressure stimuli in the area, causes the alveolar bone 30 to shrink in that area, with the subsequent loss of 40 to 60 percent of the alveolar ridge's former height measured at the gum line 50. FIG. 3 shows an endulous extraction site with loss of buccal and lingual portions of the alveolar bone 30, two years after the extraction of the tooth represented in FIG. 1. After initial 40–60% loss, the alveolar bone 30 continues to atrophy at a bone loss rate of one-half to one percent per year.

Bone replacement graft material has been used to immediately fill a socket 90 at an extraction site after a root 20 extraction, in order to promote bone growth and therefore avoid this atrophy. Bone growth is promoted via the bone graft material's intermixing with the patient's own marrow blood at the extraction site 90. While methods of applying bone graft materials to a newly extracted root site are known, a method for applying bone graft materials to an area of jaw bone which has already atrophied is not known and would have obvious benefits.

Because an application of synthetic bone replacement materials during a ridge augmentation procedure would not be preceded by a root extraction, such a method must allow the bone graft material to come into contact with the alveolar bone marrow such that the synthetic bone graft material and the alveolar bone can fuse together to create dense lamina bone a in the area where augmentation is desired. Furthermore, a method of shaping the alveolar ridge following the implantation of bone graft material in the augmentation area is required to properly maintain the shape of the implanted bone graft material consistent with the overall desired shape of the reconstructed alveolar ridge.

SUMMARY OF THE INVENTION

It is an object of the present invention to provide a method and apparatus for performing ridge augmentation on an atrophied jaw bone using synthetic or other bone replacement materials. It is a further object of the invention to provide a method and apparatus for constructing a provisional denture-stent to be used in the augmentation process either with or without implant insertion. Because the disclosed procedure involves surgery, it is also an object to provide post-operative instructions and recommended clinical follow-up procedures.

According to an aspect of the invention, a method for performing ridge augmentation on an atrophied alveolar ridge of the jaw bone of a patient utilizing synthetic bone alloplast comprises the steps of (1) constructing a denture-stent with a fitted hollow space on the underside of the stent conforming to the desired height, width and extent of ridge augmentation, (2) reflecting gingiva tissue covering the alveolar ridge at the site to be augmented, (3) inserting synthetic bone or other graft material into reflected gingiva tissue of the alveolar ridge and onto the bleeding cortical plate of the jaw bone in the area where ridge augmentation is desired, (4) suturing the reflected gingiva tissue, (5) placing the preconstructed stent over the area of the alveolar ridge containing the synthetic bone graft material immediately after the area has been sutured and (6) fixing the stent denture to the jaw bone when necessary.

BRIEF DESCRIPTION OF THE DRAWINGS

Other objects and features of the present invention will be described hereinafter in detail by way of certain preferred embodiments with reference to the accompanying drawings, in which:

FIG. 4b is a cross-sectional view of a stone or plaster model of the atrophied alveolar ridge of FIG. 4a;

FIG. 4c is a cross-sectional view of a final master model of the atrophied alveolar ridge of FIG. 4a;

FIG. 4e is a perspective view of the denture-stent of FIG. 4d after final try-in.

DETAILED DESCRIPTION OF THE PRESENT INVENTION

The method of augmenting an atrophied alveolar ridge with synthetic bone material is optimally described as a three phase method (Phases I, II and III). Phase I comprises the construction of a provisional denture-stent.

In Phase I, a dental surgeon (or any other individual qualified to construct a C denture-stent, e.g., a dental technician) constructs a provisional denture-stent with a "hollow" space on the underside of the stent to accommodate what will become the newly augmented ridge area. The patients existing denture is never to be used as the Phase I denture-stent. The dental surgeon constructs either a partial denture-stent or a full denture-stent depending on the extent of the augmentation. When only a part of the alveolar ridge is to be augmented, the dental surgeon makes a partial denture-stent. When the entire, or a substantial portion, of the alveolar ridge is to be augmented, the dental surgeon constructs a full denture-stent. Where the term "denture-stent" is used in the following detailed description, the reference includes both full and partial denture-stents.

Figure 4A:
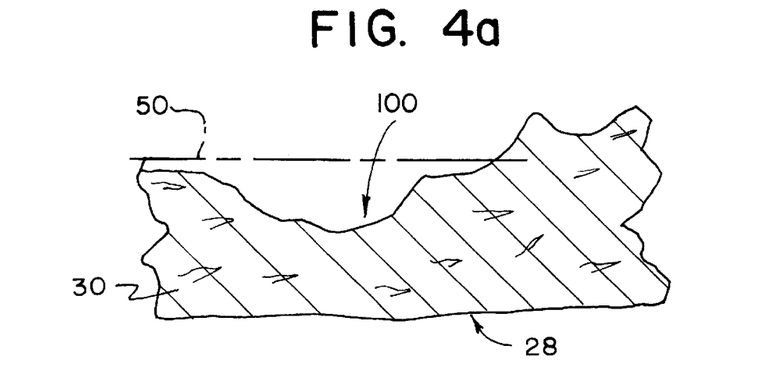
FIG. 4a is a cross-sectional view of an atrophied alveolar ridge and an area of desired augmentation.

Turning to FIGS. 4a through 4e, a method for constructing a denture-stent for use in the present invention is illustrated. With reference to FIG. 4a, a portion 28 of the patient's alveolar ridge of the lower jaw bone 30 is shown facing outward from the lingual portion of the jaw bone. As is shown, the alveolar ridge 30 is atrophied such that augmentation is desired in an area (represented by 100) between the alveolar ridge and the desired gun line 50.

Figure 4B:
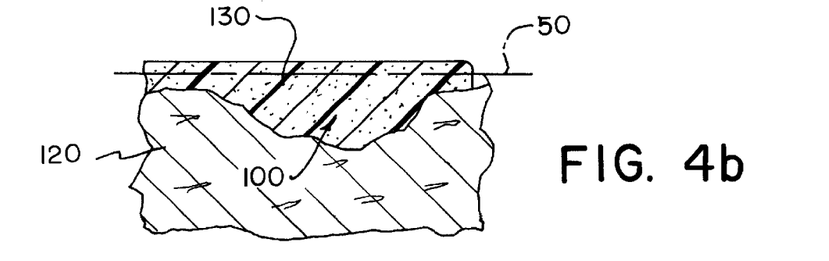

The dental surgeon commences the construction of the denture-stent in the manner known in the art. Turning to FIG. 4b, the dental surgeon constructs a stone or plaster model 120 of the atrophic alveolar ridge shown in FIG. 4a.

Model 120 is constructed using methods known in the art. With continued reference to FIG. 4b, the dental surgeon places wax on model 120 in the area representing the portion of the alveolar ridge 30 to be augmented (100). The resulting shape of the underside of the wax represents a wax impression 130 of the area of the alveolar ridge 30 to be augmented.

Figure 4C:
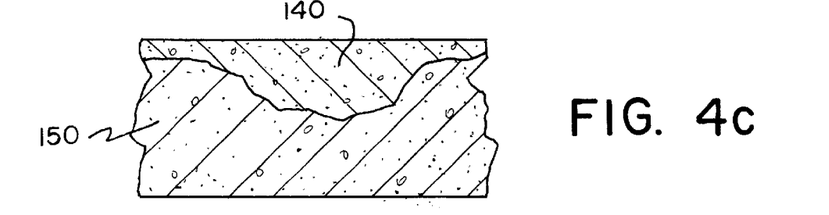

Turning to FIG. 4c, the dental surgeon uses the wax impression 130 formed in FIG. 4b to create a plaster impression 140 having the same shape as the wax impression 130 of FIG. 4b. The dental surgeon uses the plaster impression 140 to create a final master model 150 of the ridge to be augmented using methods known in the art.

Figure 4D:
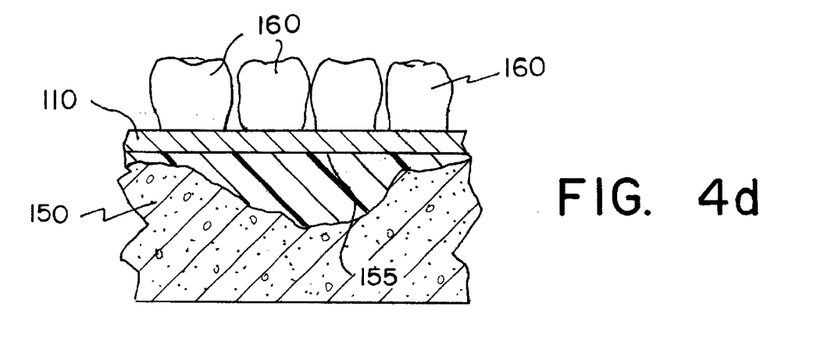
FIG. 4d is a cross-sectional view of a denture-stent formed over the final master model of FIG. 4c.

Turning to FIG. 4d, the dental surgeon constructs the denture-stent 110 over the master model 150 of FIG. 4c. As is shown, the hollow underside 155 of the denture-stent conforms to the shape of the plaster impression 140 of FIG. 4c. Further, the dental surgeon adds prosthetic teeth 160 to the top of the denture-stent 110. The denture-stent 110, at this point, is constructed of a wax and acrylic mixture.

Figure 4E:
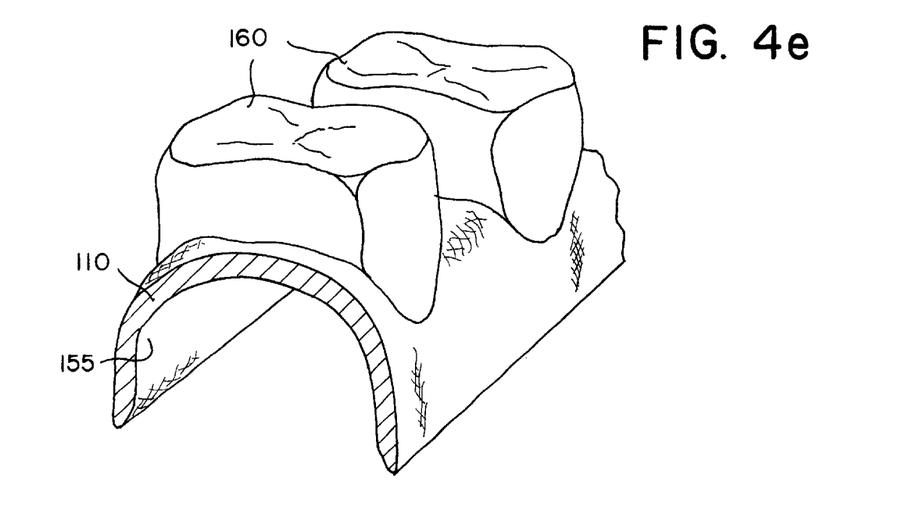

FIG. 4e represents the final denture-stent 110 prior to surgery and ridge augmentation and after final try-in of the denture-stent of FIG. 4d. As is known in the art, the final denture-stent 110 is constructed of hard acrylic or plastic. The hollow underside 155 of the final denture-stent has a shape that conforms to the shape of the desired ridge augmentation.

When the denture-stent 110 constructed on the master model is complete, it can be sterilized and the dental surgeon proceeds to Phase II of the ridge augmentation procedure. Phase II includes the surgical implantation of bone graft material into the patients atrophic alveolar ridge 30 thereby filling the hollow-space 100 with a bone replacement graft. As will be explained fully below, the denture-stent 110 is placed after the surgery is completed.

Figure 5:
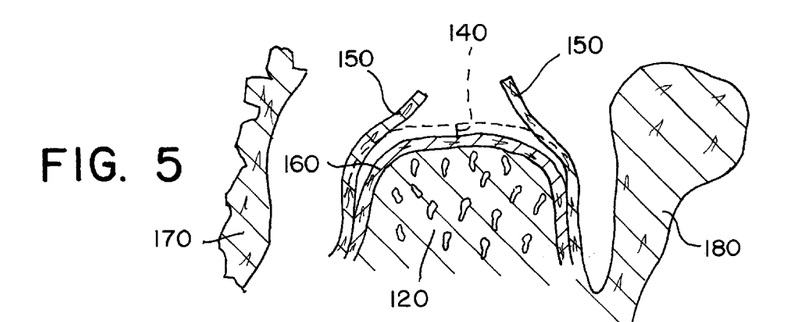
FIG. 5 is a cross-sectional view of the alveolar ridge following a full-thickness incision in the surrounding gingiva.

Turning to FIG. 5, the first step of the Phase II surgical procedure, as performed on the mandible (lower jaw bone), is illustrated. The ridge of either the maxilla (upper jaw bone) or the mandible can be augmented using this procedure. For purposes of orientation in FIG. 5, the alveolar ridge of the mandible is shown positioned between the patient s tongue 170 and the patients lip 180.

Where the mandible is to be augmented, as shown in FIG. 5, the dental surgeon makes a crestal full-thickness incision 140 in the gingiva tissue 150 at the location along the alveolar ridge where augmentation is desired. Upon reflecting the gingiva tissue 150, the cortical plate 160 of the atrophied alveolar or trabecular bone 120 is exposed. If the maxilla is to be augmented, a lingual split-thickness incision reflecting to a full-thickness incision at the crest of the ridge going in a buccal direction is made. Again, the cortical plate 160 will be exposed.

The bone graft material is now added to the exposed alveolar ridge. Although any bone graft material, such as autogenous bone or synthetics, alone or mixed with autogenous bone (e.g., Bioglass® or Bio Oss®), may be utilized as the bone graft material, prepackaged synthetic bone HTR® manufactured by Bioplant®, inc. is preferably used in Phase II of the ridge augmentation procedure. HTR® is a calcified microporous co-polymer synthetic bone alloplast which promotes bone growth by acting as a scaffold which supports the creation of dense lamina bone. Further, HTR®-24, which comprises granular particles of a larger size (750 microns in diameter), is preferably utilized. HTR-24® is prepackaged in Bioplant® 0.25 Gram straight syringes, Item #01-81002, which are available from the manufacturer. The granular form of HTR®-24 must be wetted (i.e., hydrated) in order to change the consistency of HTR® to a more useable and formable paste-like substance that will not migrate when placed on bleeding bone. The dental surgeon may additionally mix the graft material with the patient's own bone (e.g., from the hip bone) in order to promote faster and more effective growth of bone in the alveolar ridge. U.S.

patent application Ser. No. 08/831,941 describing the syringe tip and a method for using the same is hereby incorporated in its entirety by reference.

Figure 6:
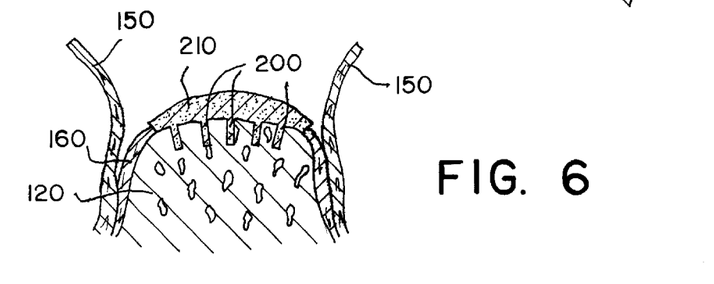
FIG. 6 is a cross-sectional view of the alveolar ridge where the cortical plate of the alveolar ridge has been punched to create bleeding marrow points.

Although the HTR® can be wetted with liquid antibiotic, liquid bone-inducer protein (e.g., BMPs), or sterile saline solution, blood from the patient's alveolar marrow is preferably used to wet the HTR®. Accordingly, as shown in FIG. 6, the dental surgeon uses a round surgical bur to punch holes 200 into the exposed cortical plate 160 of the alveolar ridge 120. The holes 200 are spaced approximately 2–4 mm apart. The use of the bur to create holes promotes marrow bleeding 210 via the small bleeding points 200 of alveolar marrow which brings to the area the precurser ("Pluri potential") cells that will form new bone.

Figures 7, 8, 9:
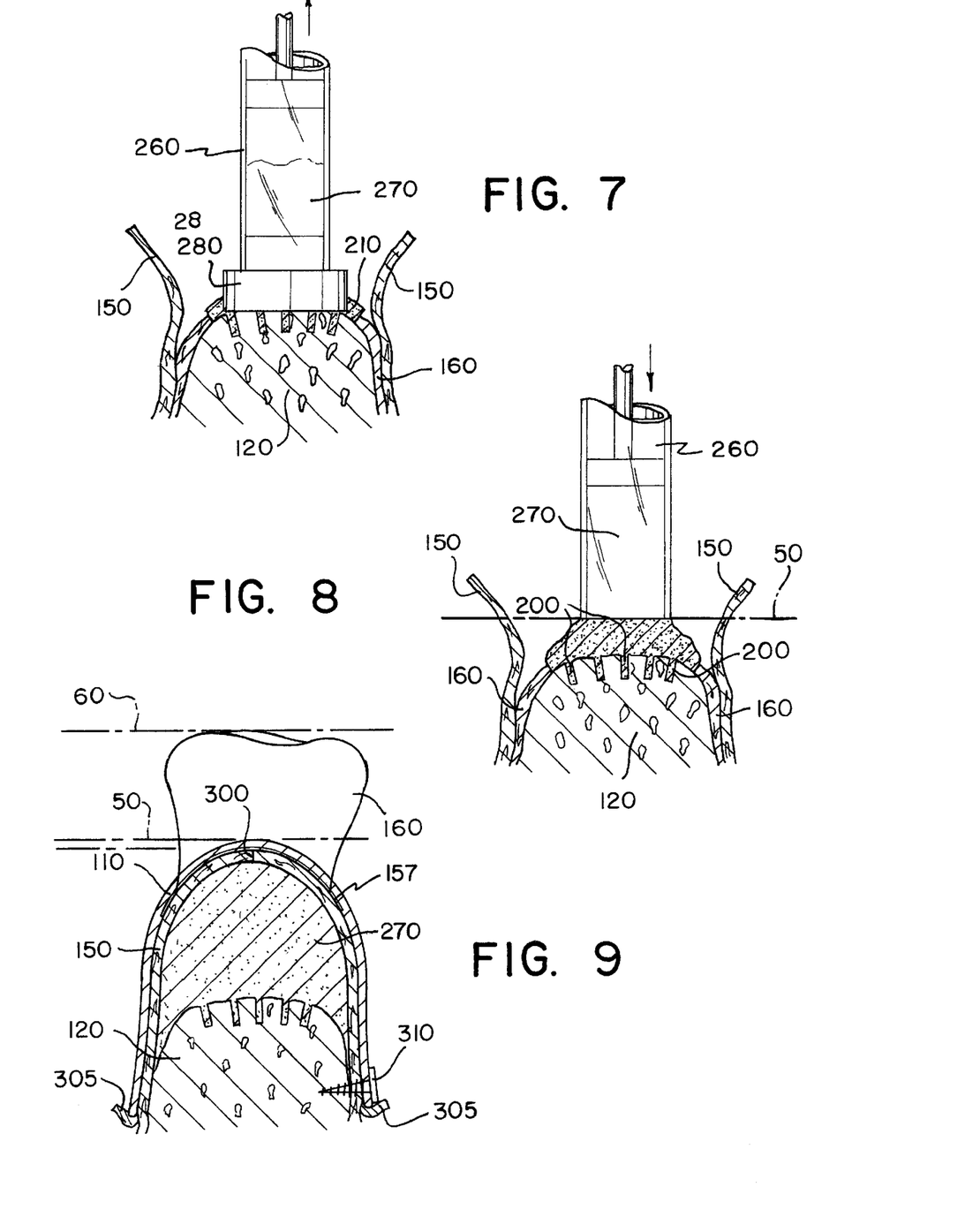
FIG. 7 is a cross-sectional view of blood from the punched bleeding points of FIG. 6 being drawn into a syringe filled with bone graft material.
FIG. 8 is a cross-sectional view of blood wetted bone graft material being applied to the bleeding cortical plate of the alveolar ridge.
FIG. 9 is a cross-sectional view of the alveolar ridge after the gingiva has been sutured and the secured dental stent has been placed over the alveolar ridge.

As shown in FIG. 7, the dental surgeon draws the bleeding marrow 210 into the syringe 260 containing granular HTR® through the syringe filter tip 280. The granular HTR® is, thereby, wetted by the blood to form a blood wetted mixture with HTR® 270. The filter 280 in the tip is sized to allow the necessary bone forming cells into the syringe 260 to mix with the graft material. Excess blood can be expelled from the syringe once a sufficient quantity of blood is mixed with the HTR®. The blood wetted HTR® 270 is permitted to congeal for three to four minutes, at the conclusion of which time the blood wetted HTR® mixture 270 will have a viscous, paste-like consistency which can more easily be formed on the alveolar ridge 120 and not migrate off the ridge 120.

As shown in FIG. 8, the dental surgeon thereafter removes the filter tip 280 of the syringe 260 and expels the wetted HTR® 270 onto the exposed and bleeding cortical plate 160. The dental surgeon expels an amount of wetted HTR® 270 sufficient to provide the required augmentation of the atrophied area of jaw bone. Because the HTR® granules are wetted, they will stay in place without migration and can be molded to generally conform with the desired width, height and shape of the alveolar ridge consistent with the gum line 50. Furthermore, by placing the wetted HTR® 270 on that portion of the cortical plate 160 where the marrow holes 200 have been punched, the wetted HTR® 270 and the alveolar marrow 280 will more readily interact to form dense lamina bone.

FIG. 9 illustrates the suture and denture-stent placement operations. Once a satisfactory amount of wetted HTR® 270 has been added to properly augment the ridge 120, the dental surgeon folds the reflected gingiva tissue 150 back over the alveolar ridge formed by the newly added wetted HTR® 270. The dental surgeon makes a primary closure 300, preferably using 3-0 silk sutures and horizontal mattress suturing. It is possible that a vertical release incision or split-thickness incision may be required in order to provide coverage of the wetted HTR® 270 and to properly heal the gingiva tissue 150.

In order for the newly augmented ridge to form properly, the dental surgeon immediately places the Phase I denture-stent 110 over the new ridge as shown in FIG. 9. If the newly augmented alveolar ridge does not sufficiently fill the hollowed space of the denture-stent, the dental surgeon relines the denture-stent 110 with a soft-line material 157. Alternately, if the newly augmented area of alveolar ridge impinges upon the hollow underside of the denture-stent, the dental surgeon relieves (removes) a portion of the denture-stent 110 adjacent to the hollow area using a large round bur on the under side soft line of the denture-stent 110.

The denture-stent 110 will hold the newly augmented ridge in shape while the alveolar bone 120 fuses with the wetted HTR® 270 to form dense lamina bone. After inserting the denture-stent 110 onto the newly augmented area of the alveolar ridge, the dental surgeon checks the fit and bite of the denture-stent. A vestibular extension 305 may be needed at this point as well as a possible frenectomy to eliminate interfering muscle attachments. Once the dental surgeon is satisfied with the present fit of the denture-stent 110, he secures the denture-stent 110 to the patient's alveolar ridge preferably using a palatal screw 310. Alternately, circumferential wiring can be used on the mandible. The screw 310 insures that the denture-stent remains in place, as it is important that the denture-stent not be removed for 7 to 10 days following the Phase II surgery in order to promote initial healing.

The present method advantageously allows the patient to immediately function with the Phase I denture-stent. The edentulous individual, who may have been unable to support a full or partial denture before the Phase II surgery, aesthetically benefits at once since the patient leaves the dental surgeon's office with a prosthesis and aesthetic tooth or teeth which are properly aligned with the gun line 50 and crown line 60. The patient never goes without teeth. Additionally, the pain and discomfort normally associated with dental surgery is minimized in that the stent acts to hold the HTR mixture in place and to prevent any remnant bleeding or trauma to the area which might occur following suturing without the denture-stent in place.

Phase of the ridge augmentation method comprises follow-up procedures. The dental surgeon instructs the patient to avoid eating solid foods for approximately 7 to 10 days. The dental surgeon also prescribes systemic antibiotics and analgesics for about 10 days. In about two days after the Phase II surgery, the dental surgeon sees the patient and inspects the patient's bite in order to be sure that the dental stent is properly mounted on the patient's alveolar ridge. Approximately 7 to 10 days following Phase II surgery, the dental surgeon removes the denture-stent 110 and cleans the surgical area using, e.g., a Peridex rinse. The denture-stent 110 is then again placed onto the patient's alveolar ridge, now as a functioning full or partial denture.

In approximately two to three months after the Phase II ridge augmentation surgery, the dental surgeon sees the patient again and inspects the effected alveolar ridge area and denture-stent 110 fitting. The dental surgeon may redo the soft-line 157 of the underside 155 of the denture-stent 110 if necessary to maintain the denture-stent's proper fit on the patient's alveolar ridge. Around six months after surgery, the dental surgeon fits the patient for a new full or partial denture in the normal manner, i.e., the dental surgeon will make a normal denture without a hollow on the underside fitting the newly restored jaw bone.

Figure 10:
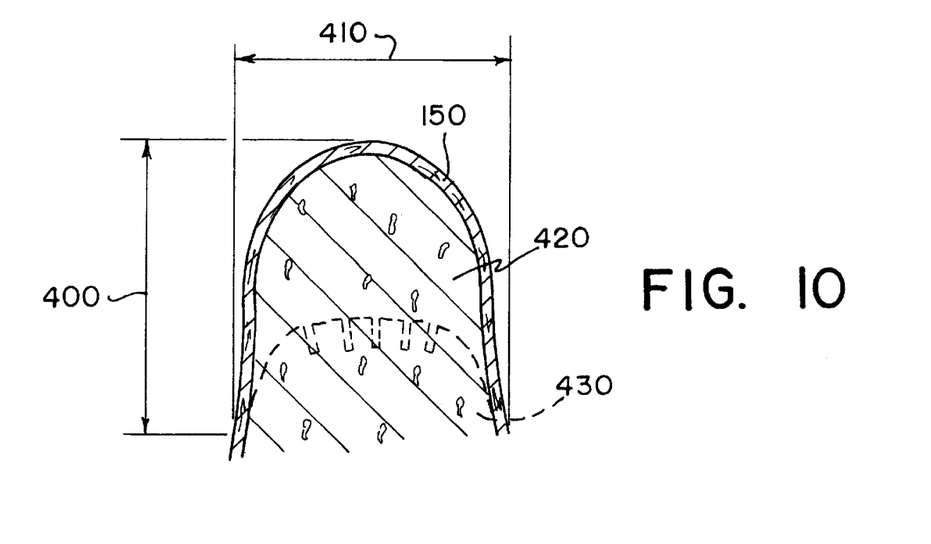
FIG. 10 is a cross-sectional view of the alveolar ridge 18 months after the marrow-wetted bone graft material is added to the alveolar ridge promoting new bone foundation and increased height and width of the alveolar ridge.
Figure 11:
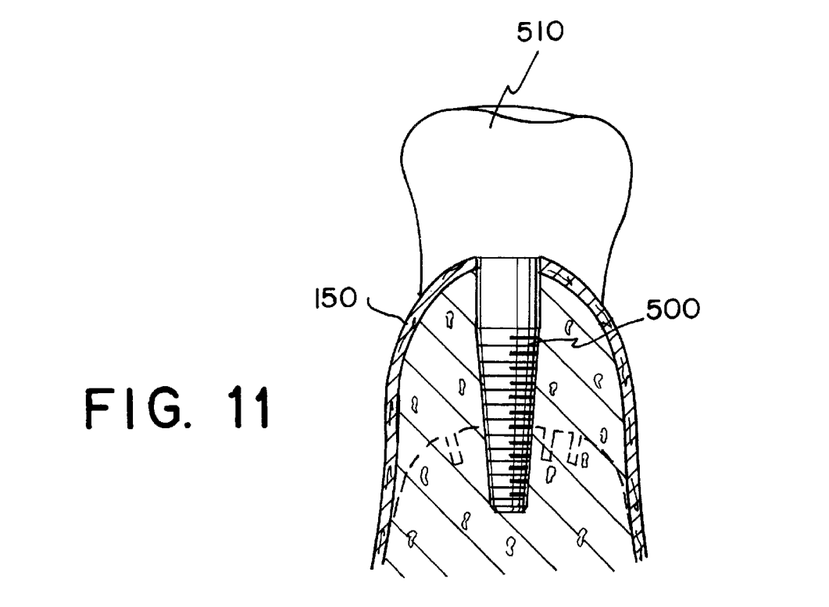
FIG. 11 is a cross-sectional view of the augmented alveolar ridge into which has been inserted an implant used to support an artificial tooth (e.g., dental implant).

FIG. 10 illustrates the augmented alveolar ridge at about 18 months after the Phase II surgery. Both the height 400 and the width 410 of the alveolar ridge increased as a result of the dense lamina bone 420 which forms over the original bony ridge 430 during the 18 month interval. At this point, the patient may continue to function normally with a full or partial denture or, as shown in FIG. 11, the patient may be considered for implant therapy whereby an implant screw 500 may be inserted into the patients' newly augmented alveolar ridge in the normal manner to support a prosthetic crown 510.

While the present invention has been particularly shown and described with reference to preferred embodiment thereof, it will be understood by those skilled in the art that various changes in form and details may be made therein without departing from the spirit and scope of the invention.

What is claimed:

1. A method for performing ridge augmentation on an atrophied alveolar ridge of the jaw bone of a patient utilizing bone graft material comprising the steps of:

creating an incision in, and reflecting, the gingival tissue on the alveolar ridge of the patient at the site of the desired ridge augmentation to expose cortical bone;

inserting wetted bone graft material against the cortical bone of the alveolar ridge of the jaw bone in the area where augmentation is desired;

forming the bone graft material into a desired height, width, extent and shape of ridge augmentation;

suturing closed the incision; and placing a denture stent over the area of said alveolar ridge prior to fusing of the alveolar bone and the bone graft material.

2. The method of claim 1 wherein said bone graft material comprises synthetic bone alloplast.

3. The method of claim 2 wherein said synthetic bone alloplast comprises a calcified microporous co-polymer.

4. The method of claim 1 wherein the step of making an incision is performed with a crestal full-thickness incision made when ridge augmentation is performed on the mandible.

5. The method of claim 1 wherein the step of making an incision is performed with a lingual split-thickness incision reflecting to a full-thickness incision at the crest of the ridge going in a buccal direction when ridge augmentation is performed on the maxilla.

6. The method of claim 1 comprising the further step of securing said stent to the patient's alveolar ridge with a palatal or surgical screw for approximately 7 to 10 days.

7. The method of claim 1, further comprising constructing the denture stent before creating the incision.

8. The method of claim 1, wherein the denture-stent is placed immediately after suturing closed the incision.

9. The method of claim 1, wherein the denture-stent has a space on the underside thereof conforming to the desired height, width and extent of ridge augmentation.

10. The method of claim 1, wherein the denture-stent holds the bone graft material in place.

11. The method of claim 1, further comprising the step of removing the denture-stent after the alveolar bone and the bone graft material fuse.

12. The method of claim 1, further comprising lining the denture-stent with a soft-line material to fill space between the denture-stent and the area of said alveolar ridge.

13. The method of claim 1 wherein the step of inserting wetted bone graft material comprises the steps of:

wetting bone graft material with the patients blood until it forms a thick paste-like material; and injecting the paste at the site.

14. The method of claim 13 wherein said blood used to wet said bone graft material is obtained from the patients cortical plate.

15. The method of claim 14 wherein holes are punched In said cortical plate with a round bur.

16. The method of claim 14 wherein the blood from the cortical plate is drawn by a syringe through the holes in the cortical plate.

17. The method of claim 16 wherein the syringe is prepackaged with bone graft material.

18. The method of claim 17 wherein the wetting of the bone graft material by the patients blood occurs inside the syringe.

19. The method of claim 13 wherein said blood is procured from the patients cortical plate by punching holes into the cortical plate.

20. The method of claim 13 wherein the mixture of bone graft material and the patients blood is allowed to congeal for three to four minutes prior to insertion at the site to allow it to form a thick paste-like form.

21. A method for performing ridge augmentation on an atrophied alveolar ridge of the jaw bone of a patient utilizing bone graft material comprising the steps of:

creating an incision in, and reflecting, the gingival tissue on the alveolar ridge of the patient at the site of the desired ridge augmentation to expose cortical bone;

inserting wetted bone graft material against the cortical bone of the alveolar ridge of the jaw bone in the area where augmentation is desired by wetting bone graft material with the patient's blood until it forms a thick paste-like material and injecting the paste at the site;

forming the bone graft material into a desired high, width, extent and shape of ridge augmentation;

suturing close the incision; and placing over area of said alveolar ridge a denture-stent with a space on the underside thereof conforming to the desired height, width and extent of ridge augmentation after said area has been sutured.

22. The method of claim 21 wherein said blood used to wet said bone graft material is obtained from the patient's cortical plate.

23. The method of claim 22 wherein said blood is procured from the patient's cortical plate by punching holes into the cortical plate.

24. The method of claim 23 wherein holes are punched in said cortical plate with a round bur.

25. The method of claim 23 wherein the blood from the cortical plate is drawn by a syringe through the holes in the cortical plate.

26. The method of claim 25 wherein the syringe is prepackaged with bone graft material.

27. The method of claim 26 wherein the wetting of the bone graft material by the patient's blood occurs inside the syringe.

28. The method of claim 21 wherein the mixture of bone graft material and the patient's blood is allowed to congeal for three to four minutes prior to insertion at the site to allow it to form a thick paste-like form.

29. A method for constructing a denture-stent for an atrophied area of a jawbone comprising the steps of:

a) constructing a model of said atrophied area of said jawbone;

b) placing wax on an atrophied area of said model corresponding to the atrophied area of said jawbone;

c) constructing a plaster impression model of said wax;

d) constructing a final master model of said denture-stent having an underside area with a shape conforming to said plaster impression model;

e) performing try-in of the final master model on the atrophied area of said jawbone; and f) constructing a final denture-stent from said final master model.

30. The method of claim 29 wherein said model of said atrophied area of said jawbone is constructed of a material selected from the group consisting of stone and plaster.

31. The method of claim 29 wherein said final master model is constructed of a wax and acrylic mixture.

32. The method of claim 29 wherein said final denture-stent is constructed of a material selected from the group consisting of hard acrylic and plastic.

33. The method of claim 29 including the additional step of adding prosthetic teeth to said final master model.

34. A method of providing an artificial tooth for an edentulous area of a patients jaw having an atrophied alveolar ridge, comprising:
- augmenting the atrophied alveolar ridge by placing bone graft material against cortical bone under gingival tissue on the alveolar ridge and placing a denture stent over said gingival tissue prior to fusing of the alveolar bone and bone graft material to maintain the bone graft material in a desired shape of ridge augmentation until the bone graft material fuses with the alveolar bone to form an augmented alveolar ridge; and
- installing a dental implant into the augmented alveolar ridge.

35. A method for of augmenting the alveolar ridge of a patients jaw bone comprising:
- placing bone graft material against cortical bone under gingival tissue on the alveolar ridge; and
- placing a denture stent over said gingival tissue prior to fusing of the alveolar to maintain the bone graft material in a desired shape of ridge augmentation at least until the bone graft material substantially fuses with the alveolar bone.

* * * * *